(12) United States Patent
Lin et al.

(10) Patent No.: US 7,538,217 B1
(45) Date of Patent: May 26, 2009

(54) RUTHENIUM COMPLEX

(75) Inventors: Jiann-T' suen Lin, Taipei (TW);
Ying-Chan Hsu, Taipei (TW);
Yung-Sheng Yen, Taipei (TW);
Ta-Chung Yin, Taoyuan Hsien (TW)

(73) Assignees: Everlight USA, Inc., Pineville, NC (US); Academia Sinica (TW)

( * ) Notice: Subject to any disclaimer, the term of this patent is extended or adjusted under 35 U.S.C. 154(b) by 0 days.

(21) Appl. No.: 12/155,032

(22) Filed: May 29, 2008

(30) Foreign Application Priority Data

Jan. 31, 2008 (TW) ............................... 97103690 A

(51) Int. Cl.
*C07F 15/00* (2006.01)
(52) U.S. Cl. .......................................... 546/2; 556/137
(58) Field of Classification Search ..................... 546/2; 556/137

See application file for complete search history.

(56) References Cited

U.S. PATENT DOCUMENTS 5,350,644 A * 9/1994 Graetzel et al. ............. 429/111

\* cited by examiner

*Primary Examiner*—Charanjit S Aulakh
(74) *Attorney, Agent, or Firm*—Bacon & Thomas, PLLC

(57) ABSTRACT

The present invention relates to a ruthenium complex, represented by the following formula (I):

$$RuLL'X_2 \qquad (I)$$

wherein L, L' and X are defined the same as the specification. The ruthenium complex of the present invention is suitable for Dye-Sensitized Solar Cell (DSSC) and has good photoelectric characteristics.

9 Claims, 2 Drawing Sheets

RUTHENIUM COMPLEX

BACKGROUND OF THE INVENTION

1. Field of the Invention

The present invention relates to a ruthenium complex and, more particularly, a ruthenium complex suitable for Dye-Sensitized Solar Cell (DSSC).

2. Description of the Related Art

With the development of civilization, human beings in the whole world face serious problems of energy crisis and environmental pollution. One of the methods to solve these problems is to convert the solar energy into electrical energy directly by a photovoltaic solar cell. Among those solar cells, Dye-Sensitized Solar Cell is a prospective novel solar cell due to its good properties, such as low manufacturing costs, possibility of manufacture as a solar cell with large area, flexibility, light transmittance and possibility of using in the buildings.

In recent years, Grätzel et al. published a serial of articles relating to Dye-Sensitized Solar Cell (for example, O'Regan, B.; Grätzel, M. Nature 1991, 353, 737), which reveal that Dye-Sensitized Solar Cell can be applied practically. Generally, the structure of the Dye-Sensitized Solar Cell comprises a cathode, an anode, nano $TiO_2$, dye and eletrolyte. The dye in the Dye-Sensitized Solar Cell has crucial affection to the efficiency of the cell. Thus, the ideal dye has to possess properties of ability of absorbing solar spectrum in a larger range, high absorption coefficient, high-temperature stability and light stability.

Grätzel's laboratory discovered a serial of ruthenium complex used to be the dye in the Dye-Sensitized Solar Cell. In 1993, Grätzel's laboratory disclosed a Dye-Sensitized Solar Cell prepared by N3 dye, of which the efficiency was up to 10.0% (AM 1.5). The incident photon to current conversion efficiency (IPCE) of the N3 dye could reach 80% in the range of 400 nm-600 nm. Thereafter, hundreds of dyes were discovered, but none of them could have the same efficiency of N3 dye. The structure of the N3 dye is shown in the following formula (a):

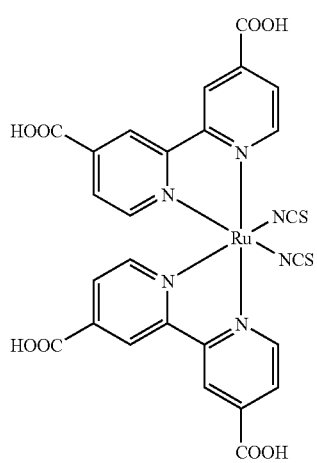

Until 2003, Grätzel's laboratory disclosed a Dye-Sensitized Solar Cell prepared by N719 dye, of which the efficiency was promoted to 10.85% (AM 1.5). The structure of N719 dye is the following formula (b):

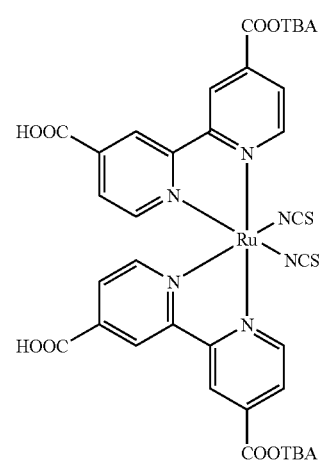

In 2004, Grätzel's laboratory disclosed a Dye-Sensitized Solar Cell prepared by Black dye, of which the efficiency was 11.04% (AM 1.5). The Black dye can strengthen the spectrum response of red light area and infrared light area so that the efficiency of the dye-sensitized cell is improved. The structure of the Black dye is shown as the following formula (c):

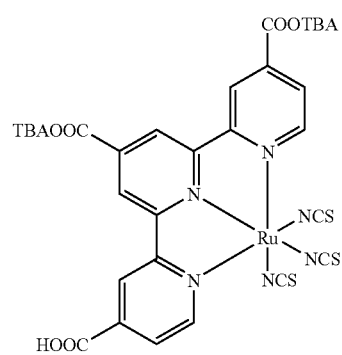

Except for the ruthenium complex of N3 dye, N719 dye and Black dye disclosed by Grätzel's laboratory, there are several similar complexes, such as platinum complex, osmium complex, iron complex, copper complex, and so on. However, numerous researches show that the efficiency of the ruthenium complex is better.

The dye in the Dye-Sensitized Solar Cell has crucial affection to the efficiency of the cell. Therefore, one of the methods to improve the efficiency of the Dye-Sensitized Solar Cell is to find a dye molecule that could improve the efficiency of the Dye-Sensitized Solar Cell.

SUMMARY OF THE INVENTION

The present invention provides a novel ruthenium complex, which is suitable for Dye-Sensitized Solar Cell.

The ruthenium complex of the present invention is represented by the following formula (I):

$$RuLL'X_2 \qquad (I)$$

wherein X is —NCS, —SCN, —SeCN, —CN or —Cl;

L is

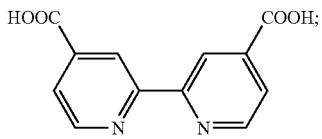

L' is

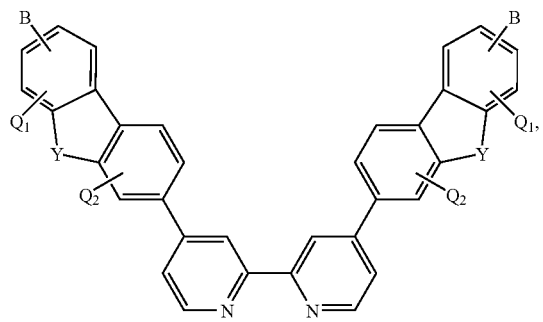

wherein

Y is —O—, —S—, —SO$_2$—, —CF$_2$—, —CCl$_2$— or —C(R$_1$)$_2$—, wherein R$_1$ is aliphatic group or aromatic group, Q$_1$ and Q$_2$ each independently is halogen, H, —CN, —SCN, —NCS or —SF$_5$, B is H or —(Z—A)$_m$—R$_2$, wherein Z is a single bond, —CF$_2$O—, —OCF$_2$—, —CH$_2$CH$_2$—, —CF$_2$CF$_2$—, —CF$_2$CH$_2$—, —CH$_2$CF$_2$—, —CHF—CHF—, —C(O)O—, —OC(O)—, —CH$_2$O—, —OCH$_2$—, —CF=CH—, —CH=CF—, —CF=CF—, —CH=CH— or —C≡C—, A is substituted or unsubstituted 1,4-phenylene, wherein one or two of =CH— can be substituted by =N—, R$_2$ is H, hydroxyl or organic group having 1 to 15 carbon atoms, m is 0, 1 or 2.

In the above formula (I), X can be —NCS, —SCN, —SeCN, —CN or —Cl; preferably, X is —NCS, —SCN, or —CN, and more preferably, X is —NCS or —SCN.

In the above formula (I), Y can be —O—, —S—, —SO$_2$—, —CF$_2$—, —CCl$_2$— or —C(R$_1$)$_2$—, wherein R$_1$ is aliphatic group or aromatic group; preferably, Y is —O—, —S—, —CF$_2$—, —CCl$_2$- or —C(R$_1$)$_2$—, wherein R$_1$ is aliphatic group or aromatic group; more preferably, Y is —CF$_2$—, —CCl$_2$— or —C(R$_1$)$_2$—, wherein R$_1$ is aliphatic group or aromatic group, and most preferably, Y is —C(R$_1$)$_2$—, wherein R$_1$ is aliphatic group or aromatic group.

The above-mentioned R$_1$ can be aliphatic group or aromatic group, and it is preferable alkyl group or alkoxy group.

In the above formula (I), Q$_1$ and Q$_2$ each independently is halogen, H, —CN, —SCN, —NCS or —SF$_5$; preferably, Q$_1$ and Q$_2$ each independently is halogen, H, or —CN, and more preferably, is halogen or H.

In the above formula (I), B can be H or —(Z—A)$_m$—R$_2$, wherein Z is a single bond, —CF$_2$O—, —OCF$_2$—, —CH$_2$CH$_2$—, —CF$_2$CF$_2$—, —CF$_2$CH$_2$—, —CH$_2$CF$_2$—, —CHF—CHF—, —C(O)O—, —OC(O)—, —CH$_2$O—, —OCH$_2$—, —CF=CH—, —CH=CF—, —CF=CF—, —CH=CH— or —C≡C—, A is substituted or unsubstituted 1,4-phenylene, wherein one or two of =CH— can be substituted by =N—, R$_2$ is H, hydroxyl or organic group having 1 to 15 carbon atoms, m is 0, 1 or 2; preferably, B is H.

The above-mentioned Z can be a single bond, —CF$_2$—, —OCF$_2$—, —CH$_2$CH$_2$—, —CF$_2$CF$_2$—, —CF$_2$CH$_2$—, —CH$_2$CF$_2$—, —CHF—CHF—, —C(O)O—, —OC(O)—, —CH$_2$O—, —OCH$_2$—, —CF=CH—, —CH=CF—, —CF=CF—, —CH=CH— or —C≡C—; preferably, Z is a single bond, —CH$_2$CH$_2$—, —C(O)O—, —OC(O)—, —CH$_2$O—, —OCH$_2$—, —CH=CH— or —C≡C—; more preferably, Z is a single bond, —CH$_2$CH$_2$—, —CH$_2$O—, —OCH$_2$—, —CH=CH— or —C≡C—; and most preferably, Z is a single bond, —CH$_2$CH$_2$— or —CH=CH—.

The above-mentioned A can be 1,4-phenylene with 1 to 4 substituents or without substituent, wherein one or two of =CH— can be substituted by =N—; preferably, A is 1,4-phenylene with 1 to 4 substituents or without substituent, of which the substituents are selected from hydroxyl, halogen, alkyl, alkoxy, alkenyl, or —CN, and more preferably, A is 1,4-phenylene with 1 to 4 substituents or without substituent, of which the substituents are selected from halogen, alkyl, alkoxy or —CN.

The above-mentioned R$_2$ can be H, hydroxyl or organic group having 1 to 15 carbon atoms; preferably, R$_2$ is H, alkyl, alkoxy, alkenyl, or —CN, and more preferably, R$_2$ is H, alkyl, alkoxy or —CN.

The above-mentioned m can be 0, 1 or 2, and preferably, m is 0 or 1.

The examples of the ruthenium complex of formula (I) includes:

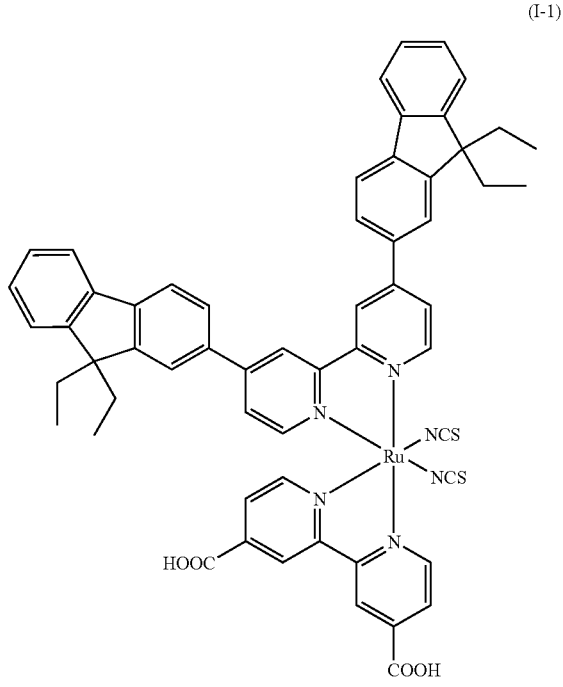

(I-1)

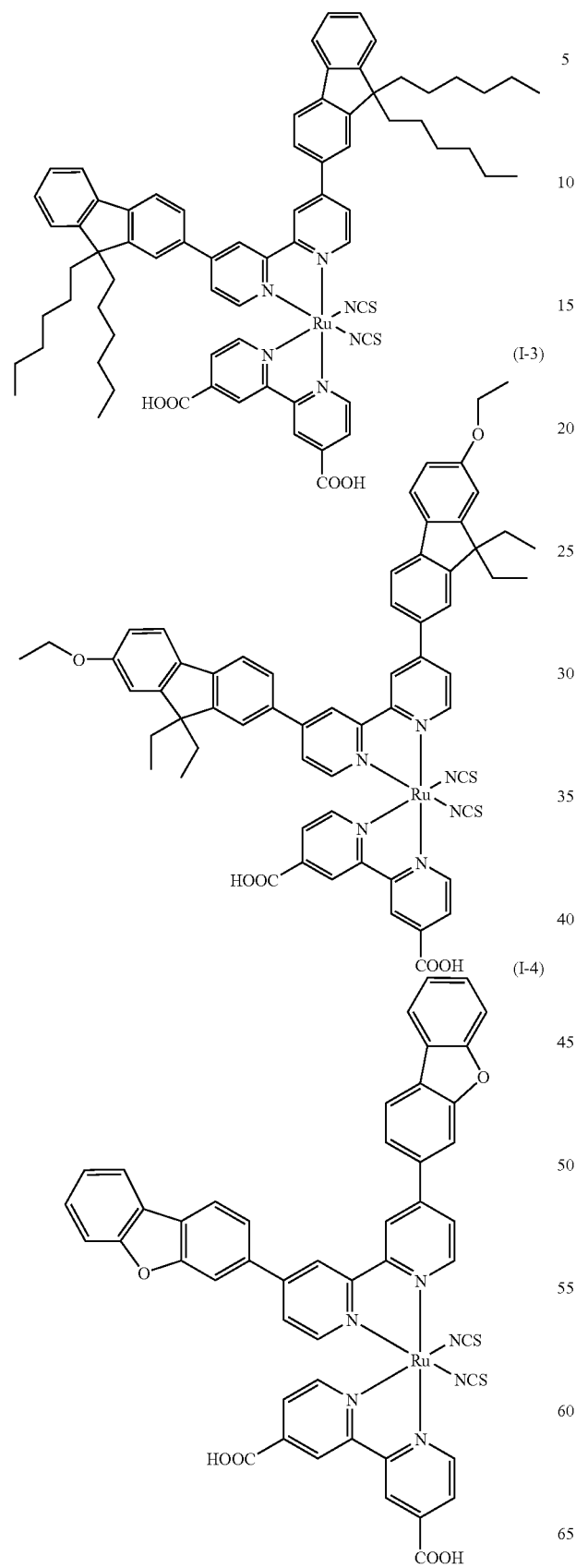
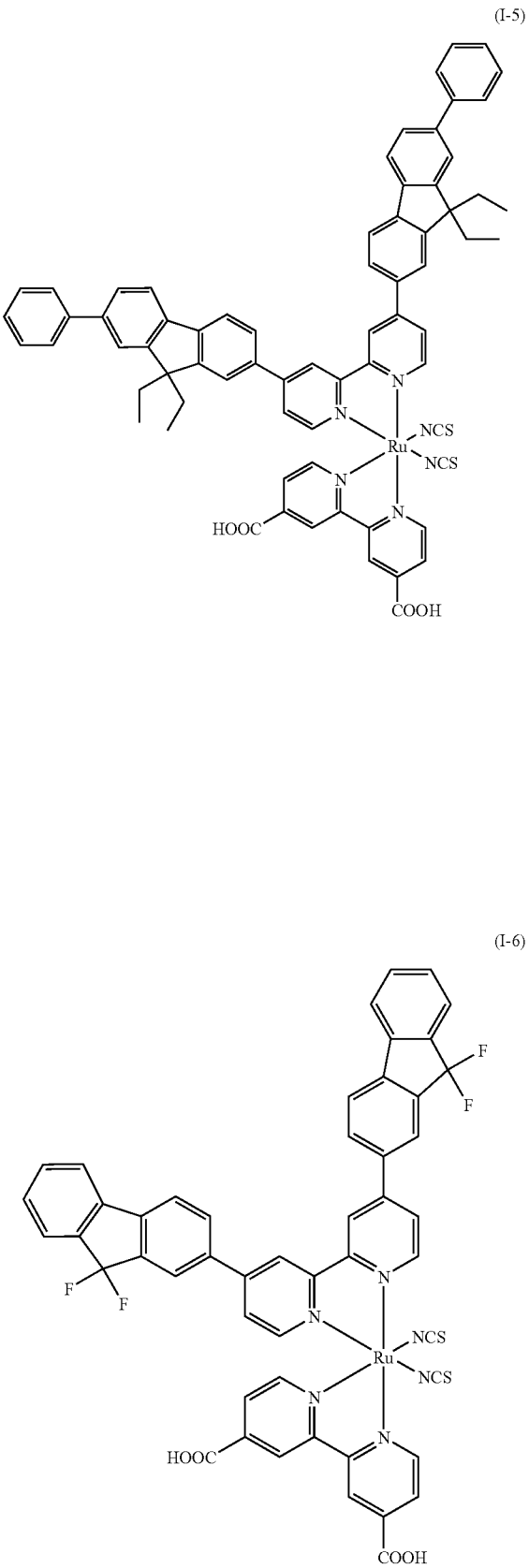

-continued (I-7)

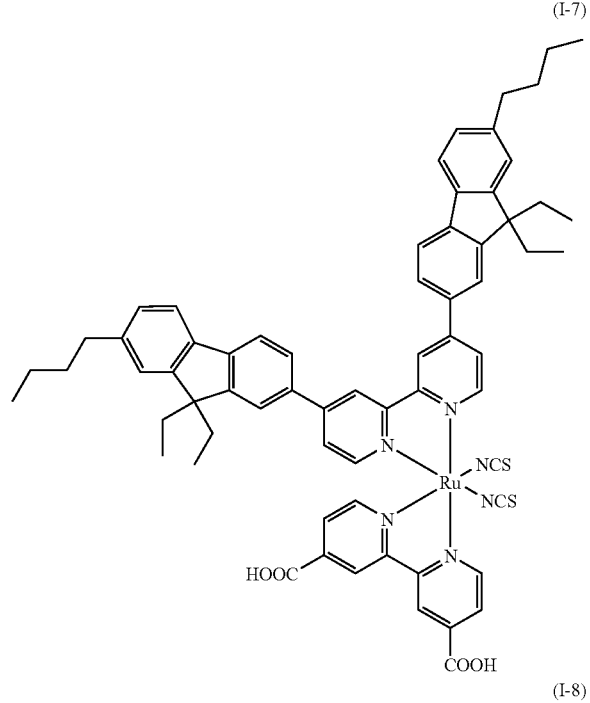

(I-8)

In the present invention, the molecule of the compound can be presented in form of free acid. However, its actual form could be salt, and more likely, could be alkaline metal salt or quaternary ammonium salt.

DETAILED DESCRIPTION OF THE PREFERRED EMBODIMENT

Figure 1:
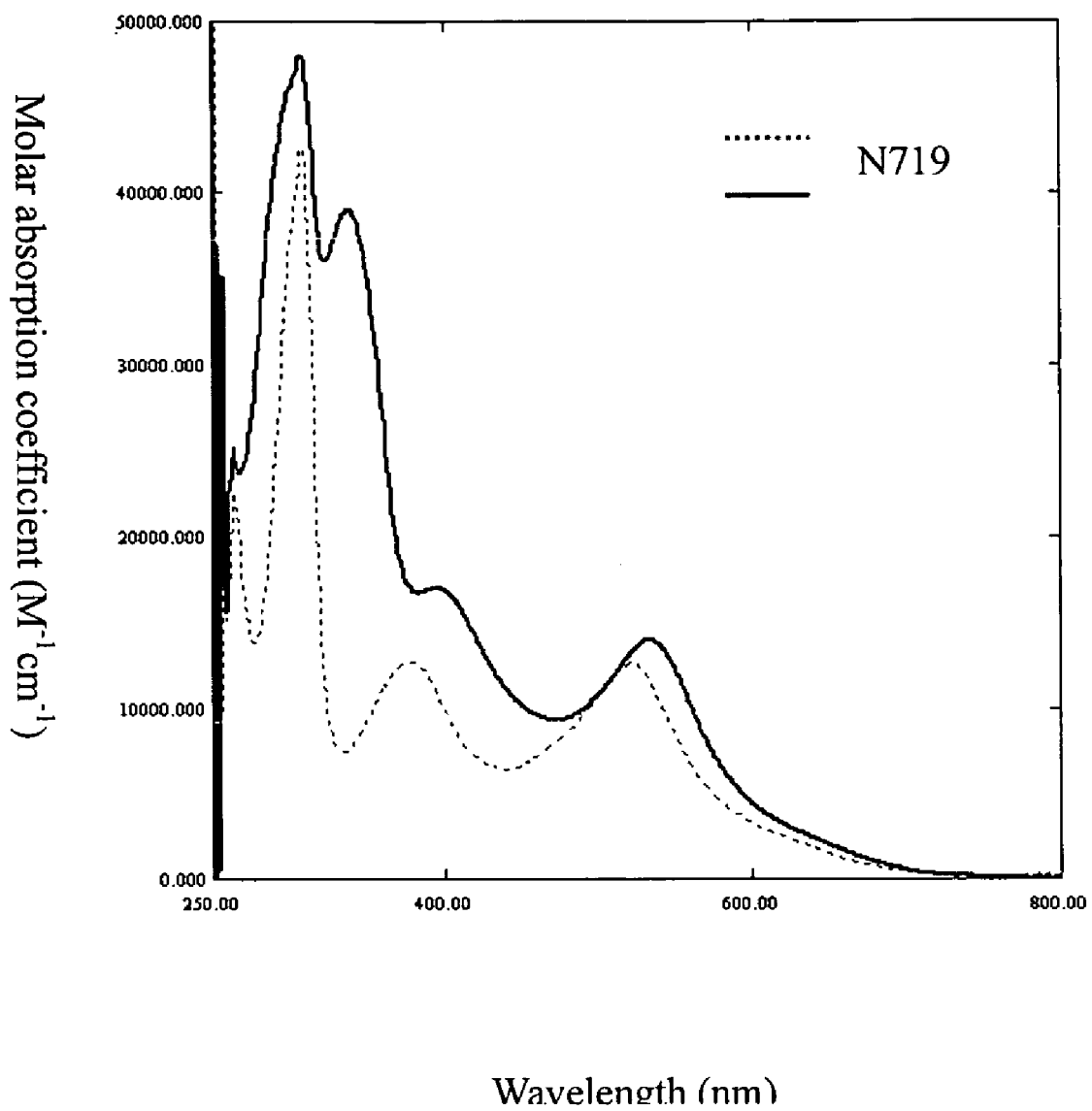
FIG. 1 is a UV-Vis absorption spectrum of the Example and the Comparative Example of the present invention.

The ruthenium complex of the present invention can be synthesized by the method of the following Process 1.

Process 1: (DMF reprensents dimethyl formamide)

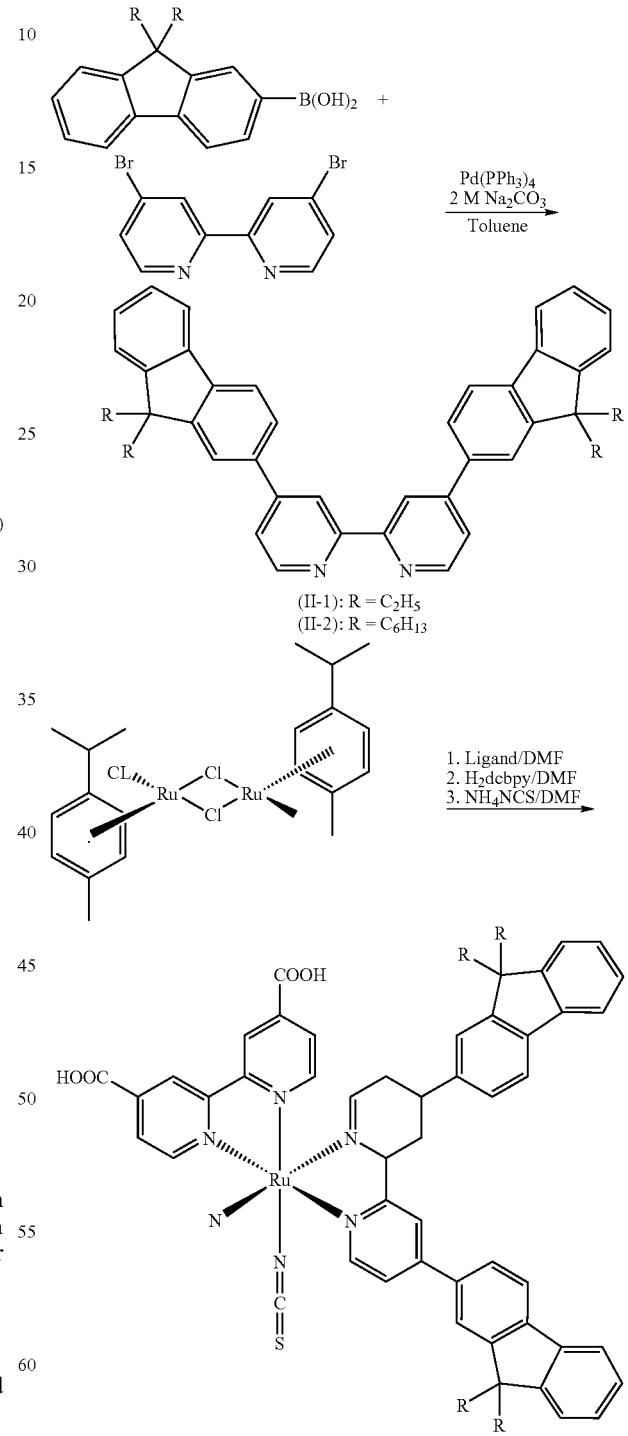

(II-1): R = $C_2H_5$
(II-2): R = $C_6H_{13}$

Firstly, 9,9-diethyl-9H-fluoren-2-ylboronic acid was reacted with 4,4'-dibromo-2,2'-bipyridine by Suzuki coupling reaction, using tetrakis(triphenylphosphine)palladium as a catalyst, to obtain a ligand of formula (II-1).

Secondly, [RuCl$_2$(p-cymene)]$_2$ and the ligand of formula (II-1) were dissolved in dehydrated dimethyl formamide and heated to 80° C. for four hours under nitrogen atmosphere to obtain a mixture. Subsequently, 4,4'-dicarboxylic acid-2,2'-bipyridine (H$_2$dcbpy) was added into the mixture and heated to 160° C. for another four hours. The aforementioned steps must be processed in the dark to prevent the generation of isomer through isomerization reaction caused by light illumination. Then, excess ammonium thiocyanate (NH$_4$NCS) was added into the mixture, and the reaction temperature was adjusted to 130° C. for five hours to obtain a ruthenium complex of formula (I-1).

The present invention will be further explained by the following examples; however, these examples are only for illustrated, but not to limit the scope of the present invention. In the examples, the compound molecule is represented in the form of free acid and its actual form could be salt, especially alkaline metal salt or quaternary ammonium salt. If there is no specific indication, then the temperature is presented by centigrade degree (° C.), the unit of the part and percentage are calculated by weight. The relation of part by weight and volume fraction is similar to that of kilogram and liter.

Example 1

Synthesis of Ligand 1.00 part of 9,9-diethyl-9H-fluoren-2-ylboronic acid, 0.42 parts of 4,4'-dibromo-2,2'-bipyridine and 0.09 parts of tetrakis(triphenylphosphine) palladium were added into 50 parts of toluene under stirring to obtain a mixture. Then, 5.64 parts of 2 M sodium carbonate aqueous solution was added into the mixture and heated to 100° C. for twelve hours. The resulted production was extracted using dichloromethane, water washed and then dehydrated using magnesium sulfate. The remnants after the dehydration were eluted, chromatographed and purified by dichloromethane/methanol in a silica gel column to obtain the ligand of formula (II-1) of the present invention.

Example 2

Synthesis of Ruthenium Complex

Under nitrogen atmosphere, 0.10 parts of [RuCl$_2$(p-cymene)]$_2$ and 0.20 parts of the ligand of formula (II-1) were dissolved in 30 parts of dehydrated dimethyl formamide and heated to 80° C. for four hours to obtain a mixture. Subsequently, 0.08 parts of 4,4'-dicarboxylic acid-2,2'-bipyridine (H$_2$dcbpy) was added into the mixture and heated to 160° C. for four hours. The aforementioned steps must be processed in the dark to prevent the generation of isomer through isomerization reaction caused by light illumination. Then, 0.98 parts of ammonium thiocyanate (NH$_4$NCS) was added into the mixture, and the reaction temperature was adjusted to 130° C. for five hours to proceed a reaction. When the reaction is finished, the solvent of the mixture was evaporated by a rotary-evaporator. Then, a great amount of water was added thereto to dissolve residual ammonium thiocyanate. Further, the resultant was filter by a sintered glass filter to collect the products insoluble in water. Further, the collected products were washed with distilled water and diethyl ether, respectively, to obtain crude products. Then, the crude products were dissolved in methanol and eluted, isolated and purified using methanol in a Sephadex LH-20 column. The eluent of main components was collected and condensed. Finally, a few drops of 0.01 M nitric acid aqueous solutions was added thereto to separate out the ruthenium complex of the formula (I-1) of the present invention.

Example 3

Synthesis of Ligand 1.42 parts of 9,9-dihexyl-9H-fluoren-2-ylboronic acid, 0.42 part of 4,4'-dibromo-2,2'-bipyridine and 0.09 parts of tetrakis(triphenylphosphine) palladium were added into 50 parts of toluene under stirring to obtain a mixture. Then, 5.64 parts of 2 M sodium carbonate aqueous solution was added into the mixture by means of a syringe and heated to 100° C. for twelve hours. Further, the resulted production was extracted using dichloromethane, water washed and dehydrated using magnesium sulfate. The remnants after the dehydration were eluted, chromatographed and purified by dichloromethane/methanol in a silica gel column to obtain the ligand of formula (II-2) of the present invention.

Example 4

Synthesis of Ruthenium Complex

Under nitrogen atmosphere, 0.10 parts of [RuCl$_2$(p-cymene)]$_2$ and 0.28 parts of the ligand of formula (II-2) were dissolved into 30 parts of dehydrated dimethyl formamide and heated to 80° C. four hours. Subsequently, 0.08 parts of 4,4'-dicarboxylic acid-2,2'-bipyridine was added thereto and heated to 160° C. for another four hours. The aforementioned steps must be proceeded in the dark to prevent the production of isomer through isomerization reaction caused by light illumination. Then, 0.98 parts of ammonium thiocyanate was added thereto, and the reaction temperature was adjusted to 130° C. for five hours to proceed a reaction. When the reaction is finished, the solvent of the mixture was evaporated by a rotary-evaporator. Further, a great amount of water was added thereto to dissolve the residual ammonium thiocyanate. Subsequently, the mixture was filted using a sintered glass filter to collect the products insoluble in water. Then, the products were washed with distilled water and diethyl ether, respectively, to obtain crude products. Further, the crude products were dissolved in methanol and eluting, isolating and purifying the solution by methanol in a Sephadex LH-20 column. The eluent of main components were collected and condensed. Finally, a few drops of 0.01 M nitric acid aqueous solutions were added thereto separate out the ruthenium complex of the formula (I-2) of the present invention.

Testing Methods and Results

UV-Vis Spectrum

Using dimethyl formamide as a solvent, the ruthenium complex dye of the present invention and N719 dye were formulated into dye solutions with concentration of 1.75×10$^{-5}$ M for measuring the UV-Vis spectrum thereof.

Manufacture and Test of the Dye-Sensitized Solar Cell

An electrode comprising TiO$_2$ nano crystalline particles were soaked in a solution containing the ruthenium complex dye of the present invention for a period of time to let the ruthenium complex dye adhere to the TiO$_2$ nano crystalline particle of the electrode. The electrode of TiO$_2$ nano crystalline particle was took out, washed slightly using a solvent, dried, and than the electrode was covered with a counterelectrode and sealed up. Then, an electrolyte (acetonitrile solution of 0.05 M $I_2$/0.5 M LiI/0.5 M t-butyl pyridine) was added therein and the injection opening was sealed up so as to obtain a Dye-Sensitized Solar Cell with effective area of 0.25 cm². The open circuit voltage ($V_{OC}$), short circuit current ($J_{SC}$), photoelectric conversion efficiency (η), filling factor (FF), and incident photon to current conversion efficiency (IPCE) of the resulted Dye-Sensitized Solar Cell were tested under the illumination of AM 1.5.

Similarly, the Dye-Sensitized Solar Cell of the N719 dye were manufactured and tested in the same manner.

The testing results are shown in the following Table 1:

TABLE 1

Testing results of the dye and the Dye-Sensitized Solar Cell

| Dye | | Molar absorption coefficient of the longest absorption wavelength ($M^{-1}cm^{-1}$) | $V_{OC}$ (V) | $J_{SC}$ (mA/cm²) | η (%) | FF |
|---|---|---|---|---|---|---|
| Example 2 | I-1 | 14007 | 0.67 | −16.56 | 7.20 | 0.65 |
| Comparative Example | N719 | 12617 | 0.69 | −16.39 | 7.12 | 0.63 |

The testing results of Table 1 show that the molar absorption coefficient of the longest absorption wavelength of the ruthenium complex of the Example 2 in the present invention is higher than that of the N719 of the Comparative Example. That is to say, the ruthenium complex of the present invention can have the same photoelectric conversion efficiency of N719 with fewer using amount.

Referring to FIG. 1, a UV-Vis absorption spectrum of the Example and the Comparative Example, it shows that the molar absorption coefficient of the ruthenium complex of the Example 2 in the present invention is higher than that of the N719 in all wavelengths. That is to say, the ruthenium complex of the present invention can have the same photoelectric conversion efficiency of N719 with fewer using amount in all wavelengths.

Figure 2:
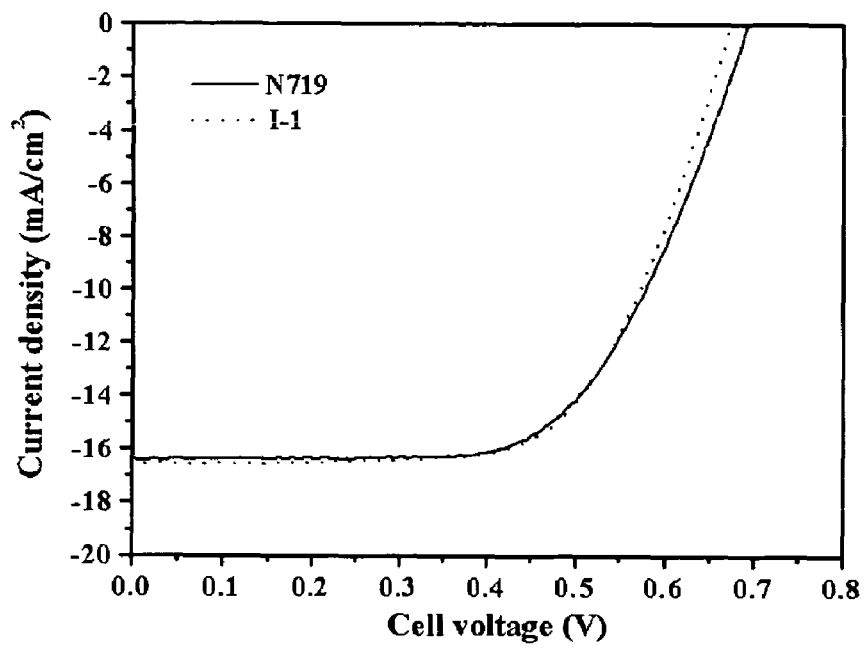
FIG. 2 is a diagram of I-V curve of the Example and the Comparative Example of the present invention.

Referring to FIG. 2, a diagram of I-V curve of the Example and the Comparative Example, it shows that the Dye-Sensitized Solar Cell prepared by the (I-1) ruthenium complex of the Example 2 of the present invention is equivalent to the Dye-Sensitized Solar Cell prepared by the N719 of the Comparative Example in every photoelectric characteristics.

Figure 3:
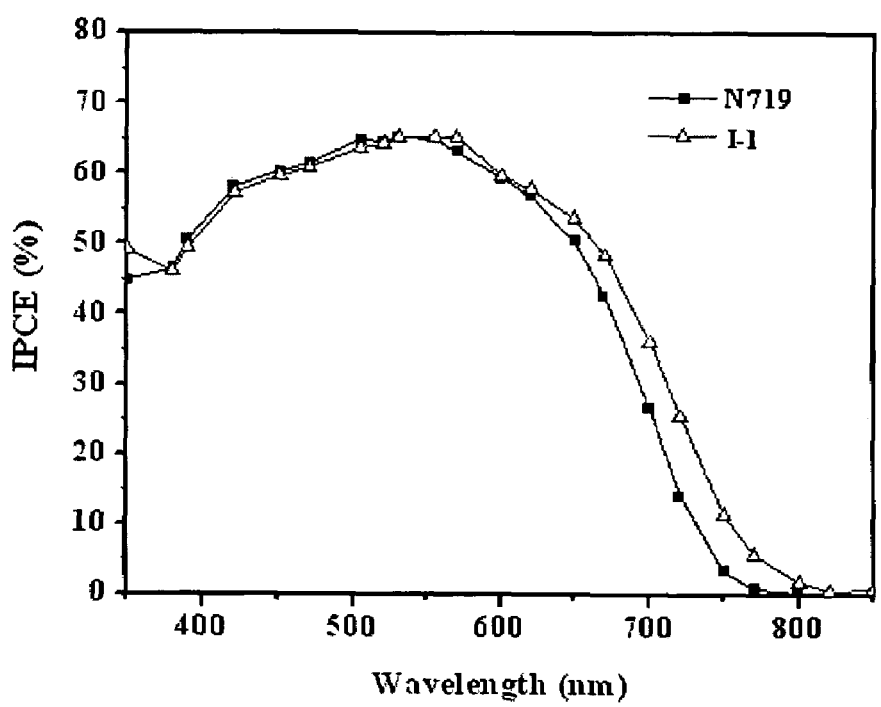
FIG. 3 is a diagram of the incident photon to current conversion efficiency (IPCE) of the Example and the Comparative Example of the present invention.

Referring to FIG. 3, a diagram of the incident photon to current conversion efficiency (IPCE) of the Example and the Comparative Example, it shows that the photoelectric conversion efficiency of the ruthenium complex of the present invention is higher than that of the N719 in long wavelength when comparing the Dye-Sensitized Solar Cell prepared by the (I-1) ruthenium complex of the Example 2 of the present invention and that prepared by the N719 of the Comparative Example.

To conclude, the present invention is different from the prior arts in several ways, such as in purposes, methods and efficiency, or even in technology and research and design. From the foregoing description, one skilled in the art can easily ascertain the essential characteristics of this invention, and without departing from the scope thereof, one can make various changes and modifications of the invention to adapt it to various usages and conditions. Thus other embodiments are also within the claim.

What is claimed is:

1. A ruthenium complex, represented by the following formula (I):

$$RuLL'X_2 \tag{I}$$

wherein X is —NCS, —SCN, —SeCN, —CN or —Cl;
L is

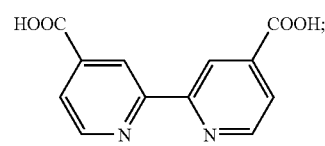

L' is

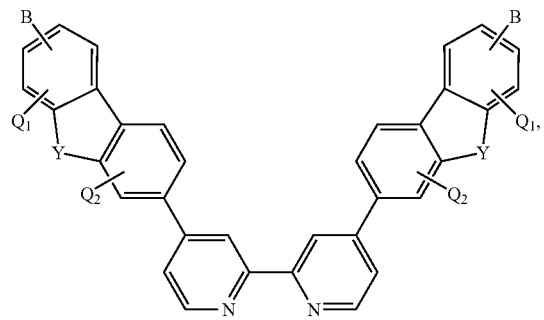

wherein
Y is —O—, —S—, —SO₂—, —CF₂—, —CCl₂— or —C(R₁)₂—, wherein R₁ is aliphatic group or aromatic group,
$Q_1$ and $Q_2$ each independently is halogen, H, —CN, —SCN, —NCS or —SF₅, B is H or —(Z—A)$_m$—R₂, wherein Z is a single bond, —CF₂O—, —OCF₂—, —CH₂CH₂—, —CF₂CF₂—, —CF₂CH₂—, —CH₂CF₂—, —CHF—CHF—, —C(O)O—, —OC(O)—, —CH₂O—, —OCH₂—, —CF═CH—, —CH═CF—, —CF═CF—, —CH═CH— or —C≡C—, A is substituted or unsubstituted 1,4-phenylene, wherein one or two of ═CH— can be substituted by ═N—, $R_2$ is H or organic group having 1 to 15 carbon atoms, m is 0, 1 or 2.

2. The ruthenium complex according to claim 1, wherein X is —NCS.

3. The ruthenium complex according to claim 1, wherein Y is —C(R₁)₂—, R₁ is aliphatic group or aromatic group.

4. The ruthenium complex according to claim 1, wherein $Q_1$ and $Q_2$ each independently is halogen, H, or —CN.

5. The ruthenium complex according to claim 1, wherein m is 0.

6. The ruthenium complex according to claim 2, wherein Y is —C(R₁)₂—, R₁ is aliphatic group or aromatic group.

7. The ruthenium complex according to claim 6, wherein $Q_1$ and $Q_2$ each independently is halogen, H, or —CN.

8. The ruthenium complex according to claim 7, wherein m is 0, R₂ is H, alkyl group or alkoxy group.

9. A ruthenium complex, represented by the following formula (I-1) or formula (I-2):
(I-1)
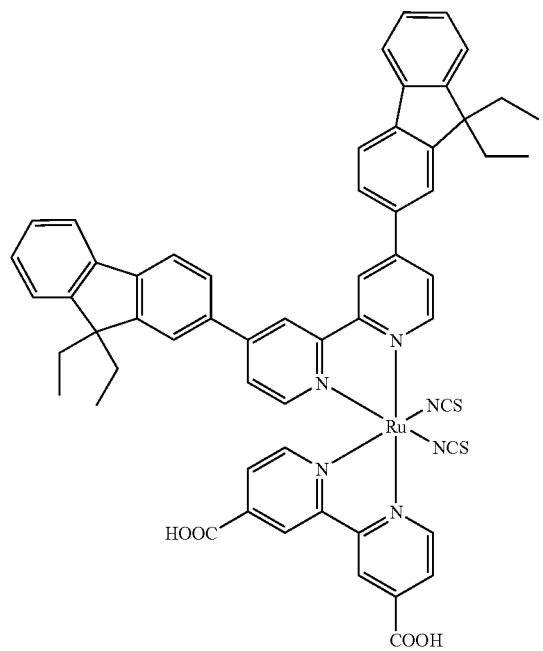
or
-continued
(I-2)
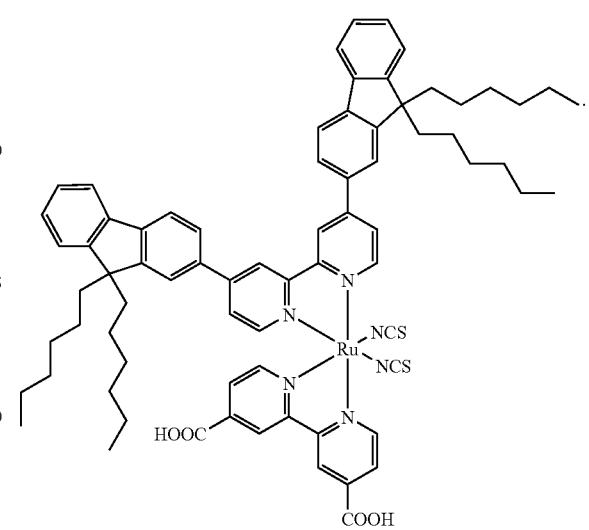
* * * * *